(12) United States Patent
Haruna et al.

(10) Patent No.: US 9,139,485 B2
(45) Date of Patent: Sep. 22, 2015

(54) PLANT TREATMENT AGENT

(75) Inventors: Ahmed Osumanu Haruna, Bintulu (MY); Latifa Omar, Bintulu (MY); Nik Muhamad Ab Majid, Bintulu (MY)

(73) Assignee: UNIVERSITI PUTRA MALAYSIA, Selangor (MY)

( * ) Notice: Subject to any disclaimer, the term of this patent is extended or adjusted under 35 U.S.C. 154(b) by 0 days.

(21) Appl. No.: 14/237,790

(22) PCT Filed: Aug. 8, 2012

(86) PCT No.: PCT/MY2012/000228
§ 371 (c)(1),
(2), (4) Date: May 23, 2014

(87) PCT Pub. No.: WO2013/022337
PCT Pub. Date: Feb. 14, 2013

(65) Prior Publication Data
US 2014/0245801 A1    Sep. 4, 2014

(30) Foreign Application Priority Data
Aug. 9, 2011 (MY) .......................... PI 2011003712

(51) Int. Cl.
| | |
|---|---|
| *C05F 11/02* | (2006.01) |
| *C05C 9/00* | (2006.01) |
| *C05G 3/08* | (2006.01) |
| *A01N 25/12* | (2006.01) |
| *C05G 3/00* | (2006.01) |
| *A61K 31/05* | (2006.01) |
| *A61K 31/194* | (2006.01) |

(52) U.S. Cl.
CPC *C05G 3/08* (2013.01); *A01N 25/12* (2013.01); *A61K 31/05* (2013.01); *A61K 31/194* (2013.01); *C05C 9/00* (2013.01); *C05C 9/005* (2013.01); *C05F 11/02* (2013.01); *C05G 3/0058* (2013.01)

(58) Field of Classification Search
None
See application file for complete search history.

(56) References Cited

U.S. PATENT DOCUMENTS

| | | | | |
|---|---|---|---|---|
| 2,097,457 | A | * | 11/1937 | Grether .............................. 71/24 |
| 2,101,807 | A | * | 12/1937 | Corey ................................ 71/24 |
| 2,142,965 | A | * | 1/1939 | Hale .................................. 71/29 |
| 3,617,237 | A | * | 11/1971 | Nagasawa et al. ................ 71/24 |
| 5,435,821 | A | | 7/1995 | Duvdevani et al. |
| 5,676,727 | A | | 10/1997 | Radlein et al. |
| 5,749,934 | A | * | 5/1998 | Parent et al. ....................... 71/24 |
| 6,056,801 | A | * | 5/2000 | Parent et al. ....................... 71/24 |
| 6,936,573 | B2 | | 8/2005 | Wertz et al. |
| 2005/0178177 | A1 | * | 8/2005 | Parent et al. ....................... 71/11 |
| 2008/0269053 | A1 | * | 10/2008 | Less et al. ..................... 504/101 |

FOREIGN PATENT DOCUMENTS

WO    2011005175 A1    1/2011

OTHER PUBLICATIONS

Petrus, Auldry Chaddy, et al. "Effect of K-N-Humates on Dry Matter Production and Nutrient Use Efficiency of Maize in Sarawak, Malaysia", The Scientific World Journal, 2010, vol. 10, pp. 1282-1292.
International Search Report and Written Opinion dated Mar. 22, 2013, in Application No. PCT/MY2012/000228 filed on Aug. 13, 2012.

* cited by examiner

*Primary Examiner* — Wayne Langel
(74) *Attorney, Agent, or Firm* — JCIP; Joseph G. Chu

(57) ABSTRACT

The present invention provides a slow release granule composition for the delivery of one or more plant treatment agents. The composition comprises an organic solution consisting peat soil liquid obtained from a peat material and urea. The granule composition is useful for the controlled delivery of fertilizers and nutrients to plants and as a soil amendment. Also disclosed is a method of treating a plant with a plant treatment agent, comprising applying a slow release granule composition of the present invention and a method to prepare the slow release granule composition.

9 Claims, No Drawings

PLANT TREATMENT AGENT

The present invention generally relates to the field of controlled plant treatment agents. More particularly, the present invention relates to a slow release granule composition for use as a fertilizer and/or soil amendment.

BACKGROUND OF THE INVENTION

Plant treatment agent is an agrochemically active substance or mixture thereof, whether naturally or synthetically derived, which is customary for the treatment of plants to modulate the growth, health and/or fertility thereof. Preferred plant treatment agents include, but are not limited to: pesticides (for example, acaricides, algicides, fungicides, bactericides, viricides, insecticides, aphicides, miticides, nematicides, molluscicides, and the like); gametocides; herbicides; defoliants; desiccants; plant-growth regulators (including growth hormones); fertilisers; plant nutrients; and mixtures thereof.

Preferably, the plant treatment agent maintains or enhances plant growth, health and/or fertility.

Although fertilisers in liquid form are convenient to apply, they are generally viewed as being environmentally disadvantageous due to product run-off into streams, rivers, aquifers and underground water catchments. Other forms of fertiliser may also lead to pollution problems such as eutrophication in bodies of water which are exposed to run-off from land that has been treated with the fertiliser, for example from land which has been aerially top dressed with superphosphate.

Several methods to control the release of nutrients to target plants and which significantly reduce pollution run-off have been disclosed.

In order to control ammonia volatilization and subsequently minimize the loss of ammonia, phosphoric acid and acidic phosphates have been used to control ammonia loss via reduction of microsite pH. However, apart from the high cost of amending these acidic materials, when they are mixed with urea, the end product is corrosive and such a product requires special precautions in handling and storage. Even if their use encourage formation of ammonium ions over ammonia gas, without good retention of the ammonium ions in the soil, efficient use of these ions by plants cannot be guaranteed as both ammonium and nitrate ions are subject to leaching. In addition, while plant nitrogen (N) can be decreased by the biological transformation of ammonium to nitrate, under anaerobic conditions, and nitrate can also be biologically denitrified to gases that lead to additional loss of N from soil.

In view of the above, it is advantageous to provide fertilisers that slowly release their nutrients to the target plants and which significantly reduce pollution run-off.

SUMMARY OF THE INVENTION

It is an object of the present invention to provide an improved slow release granule composition and/or to provide an improved slow release fertliser formulation.

It is another object of the present invention to provide an improved slow release fertilizer formulation that is capable of reducing ammonia loss.

It is yet another object of the present invention to provide an improved slow release fertilizer formulation that is capable of addressing the afore-mentioned problems associated with the use of inorganic acids that lack the ability to efficiently retain ammonium ions in the soil.

In a first aspect of the present invention, there is provided a slow release granule composition comprising a plant treatment agent, the slow release granule composition comprising an organic solution and urea.

The organic solution is acidic with pH less than 4 and is a peat soil water forcefully obtained from a peat material under pressure. The peat material is either fibric, hemic, or sapric. Fibric peats are the least decomposed, and comprise intact fiber. Hemic peats are somewhat decomposed, and sapric are the most decomposed.

The acidic nature of the peat soil water aids to reduce ammonia loss via reduction of soil pH. Considering the acidic nature of the peat soil water, the water can be used to reduce ammonia loss from urea. Amending urea with the peat soil water may control soil pH through inhibition or ureolytic activity of microorganisms, hence contributing to reduction of ammonia loss by encouraging formation of ammonium and nitrate ions over ammonia.

In a second aspect of the present invention, there is provided a method of treating a plant with a plant treatment agent, comprising applying a slow release granule composition the present invention.

In a third aspect of the present invention, there is provided a method to prepare a slow release granule composition comprising a plant treatment agent, the method comprising the steps of:
i. separating immiscible liquids or solids contained in a solution of peat soil water; and
ii. equilibrating the peat soil liquid obtained in step (i) with urea wherein the mixture is agitated at 180 rpm to 250 rpm to obtain a slow release granule composition, in which part of K and N are in the form of K-humate, K-fulvate, N-humate, and N-fulvate.

Besides reducing ammonia loss from urea, the slow release granule composition of the present invention provides an alternative means of improving urea-N use efficiency in both waterlogged and non water soils by amending it with peat water. Mixing urea with peat soil water significantly reduces ammonia loss compared with urea alone as this method encourages formation of exchangeable ammonium and available nitrate over ammonia. In addition to ensuring readily available soil exchangeable cations (Ammonium, potassium, and magnesium), available nitrate, available P and total N for plant use, the present invention also ensures significant dry matter production, N, P, and K uptake and their use efficiency. Urea-N use efficiency could be improved by reducing ammonia loss by amending urea with peat water because this approach ensures reduction of microsite pH of applied urea by peat soil water as well as enhancing ammonium ions retention and timely release for plant uptake.

DETAILED DESCRIPTION OF THE INVENTION

The present invention provides a slow release granule composition that allows the encapsulation of a large variety of natural and synthetic plant treatment agents to produce a number of useful formulations. Advantageously, the slow release granule composition also acts as a soil amendment.

The term "plant treatment agent" as used herein means any agrochemically active substance or mixture thereof, whether naturally or synthetically derived, which is customary for the treatment of plants to modulate the growth, health and/or fertility thereof. Preferred plant treatment agents include, but are not limited to: pesticides (for example, acaricides, algicides, fungicides, bactericides, viricides, insecticides, aphicides, miticides, nematicides, molluscicides, and the like); gametocides; herbicides; defoliants; desiccants; plant-growth regulators (including growth hormones); fertilisers; plant nutrients; and mixtures thereof.

Preferably, the plant treatment agent maintains or enhances plant growth, health and/or fertility.

More preferably, the plant treatment agent comprises a pesticide, plant-growth regulator, fertiliser, plant nutrient or a mixture thereof.

Still more preferably, the plant treatment agent comprises a fertiliser, plant nutrient or mixture thereof.

As discussed above, fertilisers are generally formulated as liquids prior to application or are applied as water soluble solids which immediately release their nutrients to the environment upon dissolution.

In the present invention, the plant treatment agent is preferably mixed with an acidic organic solution, the acidic organic solution is liquid or waste water obtained from peat materials, under pressure.

In one embodiment, the plant treatment agent comprises a fertiliser derived from plant and/or animal sources. Examples of suitable sources include, but are not limited to: animal manure; compost and other decomposed animal and plant material; abattoir waste such as feather meal and bone meal; dairy waste such as whey; plant material such as soybean meal; seaweed; fish; and mixtures thereof.

Mixtures of fertilisers are also contemplated. The N:P:K ratio and trace element content of the fertilizer may be optimised for specific applications to provide a variety of fertilizer mixtures.

Preferably, the plant treatment agent is incorporated into the slow release granule composition as an aqueous solution, emulsion or suspension which is mixed with acidic organic solution obtained from peat materials.

Those persons skilled in the art will appreciate that the amount of plant treatment agent used in the slow release granule composition will depend on a number of factors which may include: the preferred application rate for the plant treatment agent; the concentration of the plant treatment agent or the solution thereof; and the solubility for the plant treatment agent or the solution thereof.

Soil Physico-chemical Analysis

Peat soil water (waste water) was collected from natural flows of peat water at Suai Miri Sarawak, Malaysia. The mineral soil used was Bekenu Series (Fine loamy, siliceous, isohyperthermic, red-yellow to yellow Tipik Tualemkuts). It was sampled in an undisturbed area of Universiti Putra Malaysia Bintulu Sarawak Campus, Malaysia using an auger. The soil taken at 0-15 cm depth was air dried and ground to pass 2.0 mm sieve for laboratory experiment. The soil texture was determined using the hydrometer method (Bouyoucos, 1962) and its field capacity and bulk density determined by the method described by Tan (2005). The pH of the soil was determined in a 1:2 soil:distilled water suspension and KCl using a glass electrode. However, the pH of the peat soil water was determined directly from filtered samples using a glass electrode. The soil total carbon, N and organic matter were determined using LECO CHNS Analyzer (Leco Truspec Micro Elemental Analyzer CHNS, New York). Soil available P was extracted using the double acid method (Tan, 2005) followed by blue method (Murphy and Riley, 1962). The Kjedhal method was used to determine total N. Exchangeable cations were extracted using leaching method and their concentrations were afterwards determined using followed Atomic Absorption Spectrometry (AAS). Soil CEC was determined by the leaching method followed by steam distillation.

Laboratory Evaluation of Treatments Under Waterlogged

Upon maintaining soil water at 70% field capacity using distilled water, the treatments below were evaluated:
i. Soil only (T0)
ii. 2.02 g urea (T1)
iii. 2.02 g urea+175 mL peat soil water (T2).

The quantity of urea used was based on the standard recommendation for the test crop. These materials were thoroughly mixed on a reciprocal shaker at 170 rpm for 15 minutes to ensure they were uniformly mixed.

Laboratory Evaluation of Treatments Under Non-waterlogged

The same set of treatments were prepared and mixed as previously outlined except that the liquid of the treatments were used to obtain field capacity of 70%.

Ammonia Loss Evaluation for Both Waterlogged and Non-waterlogged Conditions

The daily loss of $NH_3$ from urea was measured by using a closed-dynamic air flow system method (Siva et al., 1999; Ahmed et al., 2006a; Ahmed et al., 2006b). The system consisted of an exchange chamber of 500 mL conical flask containing 250 g soil sample and 250 mL conical flask containing 75 mL of boric acid which were both stoppered and fit with an inlet/outlet. The inlet of the chamber was connected to an air pump and the outlet was connected by polyethylene tubing which contains boric acid and indicator solution to trap ammonia gas (Ahmed et al., 2006a; Ahmed et al., 2006b). Air was passed through the chamber at the rate of 3.5/L/min/chamber. This rate of air flow was maintained throughout the incubation period using a Gilmont flow meter to measure and adjust the air flow when necessary. The released ammonia captured in a trapping solution which contains 75 mL of boric acid with bromocresol green and methyl red indicator was titrated with 0.1 M HCl to estimate the amount of $NH_3$ (g) released. The entire incubation was conducted at room temperature. The boric acid indicator which was used to capture ammonia was replaced every 24 h during incubation for 13 days, a period when ammonia loss was less than 1% (Ahmed et al., 2006a, 2006b). After 13 days of incubation, soil samples were analyzed for pH, exchangeable ammonium and available nitrate. Soil pH was determined by the method previously stated. The method of Keeney and Nelson (1982) was used to extract soil exchangeable ammonium and available nitrate followed by steam distillation. The experimental design was a completely randomized design with three replicates for each treatment. Analysis of variance was used to test treatment effects and means of treatments were compared using Duncan's test (SAS version 9.2).

Greenhouse Experiment to Scale Up Laboratory Experiment

A pot experiment was conducted in a greenhouse of Universiti Putra Malaysia Bintulu Sarawak Campus, Malaysia using randomized complete block design (RCBD) with three replications. Each pot size was 22×28 cm. Each was filled with 10 kg soil (based on bulk density of the soil). Hybrid no. 5 variety (*Zea mays* L.) was used as the test crop. Its N, P, and K requirement were 60 kg N, 60 kg $P_2O_5$ and 40 kg $K_2O$ (130 kg $ha^{-1}$ urea: 130 kg $ha^{-1}$ TSP: 67 kg $ha^{-1}$ KCl). The fertilizer requirement was scaled down to per pot basis equivalent to 2.02 g of urea, 5 g of TSP and 5 g of KCl. The volume of water used for each pot was based on field capacity (70%). The three treatments devised for this experiment were as follows:
i. No fertilizer (T0)
ii. 2.02 g urea (T1)
iii. 2.02 g urea+7 L peat soil water (T2)

All treatments were applied on the $10^{th}$ day after planting (DAP). However TSP and KCl which were common to all the treatments were applied on 10 DAP and 28 DAP. The plants were monitored until tassel stage. Tassel stage is the maximum growth stage for plants before they enter productive stage.

Harvesting was done on the 56$^{th}$ DAP. The whole plant including leaves and stem were harvested. The remaining roots in the soil were removed carefully. They were cleaned using tap and distilled water. The plant parts (leaves, stem and roots) were then oven-dried at 60° C. until constant weight was attained afterwhich they weighed using a digital balance. Soil samples were also taken from the pots, air-dried, pounded and sieved to a pass 2 mm before they were analyzed for pH, exchangeable cations (K, Mg, and Ca), total carbon, total N, available P, exchangeable ammonium and available nitrate, using standard procedures. Each plants part was ground and analyzed for total K, Mg, Ca, Na, N, and P.

Nitrogen, P and K uptake in leaves, stem and roots were determined by multiplying the concentration with the dry weight of the plant parts. Nitrogen, P and K use efficiency were determined by the formula of Pomares-Gracia and Pratt (1987).

Analysis of variance (ANOVA) was used to test the effect of treatments while means of treatments were compared using Duncan's Test. Statistical Analysis System (SAS Ver. 9.2) was used for the statistical analysis.

Physico-chemical Properties of the Mineral Soil Used in Both Laboratory and Greenhouse Experiments The selected physico-chemical properties of the mineral soil called Bekenu Series (Fine loamy, siliceous, isohyperthermic, red-yellow to yellow Tipik Tualemkuts) used in this work are summarized in Table 1. These physico-chemical properties were typical of Bekenu Series (Paramananthan, 2000).

TABLE 1

Selected physico-chemical properties of Bekenu Series

| Property | Value Obtained | Standard Data Range* |
|---|---|---|
| pH (water) | 4.11 | 4.6-4.9 |
| pH (KCl) | 3.86 | 3.8-4.0 |
| CEC (cmol kg$^{-1}$) | 7.33 | 3.86-8.46 |
| Texture | SCL | SCL |
| Bulk density (g cm$^{-3}$) | 1.51 | nd |
| Organic matter (%) | 2.28 | nd |
| Available P (mg kg$^{-1}$) | 2.39 | nd |
| Total Nitrogen (%) | 0.15 | 0.04-0.17 |
| Organic carbon (%) | 0.57 | 0.57-2.51 |
| Exchangeable Ca (mg kg$^{-1}$) | 2.05 | 0.05-0.19 |
| Exchangeable Mg (mg kg$^{-1}$) | 0.18 | 0.07-0.21 |
| Exchangeable K (mg kg$^{-1}$) | 0.16 | 0.05-0.19 |

CEC, cation exchange capacity; SCL, Sandy Clay Loam; nd, not determined.
*Standard data range (Paramananthan, 2000).

Selected Chemical Properties of Peat Soil Water and Urea

The pH of the peat soil water was acidic while the pH of urea was basic, as shown in Table 2.

TABLE 2

Selected chemical properties of peat soil water and urea

| Property | Peat Soil Water | Urea |
|---|---|---|
| pHw | 3.90 | 8.00 |
| pH (KCl) | nd | nd |
| Total Nitrogen (%) | 0.16 | nd |
| Exchangeable Ca (mg/kg) | 0.42 | nd |
| Exchangeable Mg (mg/kg) | 0.12 | nd |
| Exchangeable K (mg/kg) | 0.02 | nd |

CEC: cation exchange capacity; nd: not determined.

Total Amounts of Ammonia Lost Over 13 Days of Incubation i. Waterlogged condition The total amounts of ammonia lost at 13 days of incubation are presented in Table 3. The treatment with peat soil water (T2) significantly reduced ammonia loss compared with urea without additives (T1). At 13 days of incubation, the soil pH of T1 and T2 were not statistically different and this was because the ammonia loss at this period did not vary significantly.

TABLE 3

Total amounts of ammonia lost and soil pH from incubation under waterlogged condition

| Treatment | Ammonia loss (%) | soil pH (water) |
|---|---|---|
| T0 | 0$^c$ | 5.40$^b$ |
| T1 | 42.87$^a$ | 7.21$^a$ |
| T2 | 32.29$^b$ | 7.16$^a$ |

Means with same letter within column are not significantly different by DNMRT at p ≤ 0.05.

ii. Non-waterlogged condition

The total amounts of ammonia volatilized over the 13 days of incubation are summarized in Table 4. The treatment with peat soil water (T2) significantly reduced ammonia volatilization compared with urea without additives (T1). At 13 days of incubation, the pH of the soil treated with urea and peat soil water was significantly lower than that of urea without additives (Table 4).

TABLE 4

Total amounts of ammonia lost and soil pH over 13 days of incubation under non-waterlogged condition

| Treatment | Ammonia loss (%) | soil pH (water) |
|---|---|---|
| T0 | 0$^c$ | 5.14$^c$ |
| T1 | 41.50$^a$ | 7.68$^a$ |
| T2 | 37.44$^b$ | 7.23$^b$ |

Means with same letter within column are not significantly different by DNMRT at p ≤ 0.05.

Ammonium and Nitrate Contents at 13 Days of Incubation i. Waterlogged condition

There was a significant accumulation of soil exchangeable ammonium and available nitrate with urea amended with peat soil water compared with urea without additives, as shown in Table 5.

TABLE 5

Accumulation of exchangeable ammonium and available nitrate at 13 days of incubation

| Treatment | NH$_4$-N (ppm) | NO$_3$-N (ppm) |
|---|---|---|
| T0 | 12.07$^c$ | 1.55$^c$ |
| T1 | 78.09$^b$ | 22.80$^b$ |
| T2 | 137.44$^a$ | 27.50$^a$ |

Means with same letter within column are not significantly different by DNMRT at p ≤ 0.05.

ii. Non-waterlogged condition

There was a significant accumulation of soil exchangeable ammonium and available nitrate with urea amended with peat soil water at 13 days of incubation compared with urea alone, as shown in Table 6.

TABLE 6

Contents of exchangeable ammonium and available nitrate at 13 days of incubation under non-water logged condition

| Treatment | $NH_4^-N$ (ppm) | $NO_3^-N$ (ppm) |
|---|---|---|
| T0 | 11.98$^d$ | 2.46$^c$ |
| T1 | 85.80$^c$ | 4.30$^b$ |
| T2 | 127.44$^b$ | 4.44$^a$ |

Means with same letter within column are not significantly different by DNMRT at $p \leq 0.05$.

Greenhouse Results i. Soil exchangeable ammonium and available nitrate

There was a significant accumulation of soil exchangeable ammonium with urea amended with peat soil water at 56 days after planting (Greenhouse experiment) compared with urea alone (see Table 7).

TABLE 7

Effect of on ammonium and nitrate at 56 days after planting

| Trt | $NH_4^-N$ (ppm) | $NO_3^-N$ (ppm) |
|---|---|---|
| T0 | 18.47$^c$ | 3.67$^c$ |
| T1 | 23.40$^b$ | 5.34$^a$ |
| T2 | 31.13$^a$ | 5.43$^a$ |

Means with same letter within column are not significantly different by DNMRT at $p \leq 0.05$.

ii. Other selected soil chemical properties

With the exception of Ca and soil pH, soil exchangeable Mg, K, and available P were significantly increased with urea amended with peat soil water compared with urea alone, as shown in Table 8.

TABLE 8

Effect of treatments on selected soil chemical properties at 56 days after planting

| Trt (water) | Ca (ppm) | Mg (ppm) | K (ppm) | P (ppm) | pH |
|---|---|---|---|---|---|
| T0 | 1.28$^b$ | 1.26$^c$ | 1.28$^c$ | 0.28$^c$ | 4.58$^a$ |
| T1 | 2.32$^a$ | 2.36$^b$ | 2.63$^b$ | 0.46$^b$ | 3.94$^a$ |
| T2 | 2.62$^a$ | 3.34$^a$ | 3.09$^a$ | 1.32$^a$ | 3.89$^a$ |

Means with same letter within column are not significantly different by DNMRT at $p \leq 0.05$.

Nitrogen Uptake and Use Efficiency in Maize Plant

A reflection of the effectiveness of amending urea with peat soil water in improving urea-N use is demonstrated in Tables 10 and 11 where T2 significantly improved N uptake and use efficiency in the parts of the test crop compared with that of urea alone. Similar observation was not glaring for P and K as the results were inconsistent.

TABLE 9

Effect of treatments on dry weight of maize plant at 56 days after planting

| Trt | Stems | Leaves | Roots (g plant$^{-1}$) | Total |
|---|---|---|---|---|
| T0 | 5.37$^d$ | 4.23$^c$ | 3.14$^b$ | 12.74$^c$ |
| T1 | 5.71$^d$ | 6.00$^b$ | 3.18$^b$ | 14.89$^b$ |
| T2 | 6.46$^c$ | 6.33$^a$ | 4.62$^a$ | 17.41$^a$ |

Means with same letter within column are not significantly different by DNMRT at $p \leq 0.05$.

TABLE 10

Effect of treatments on N, P, and K uptake of maize plant at 56 days after planting

| Trt | N | P | K | (%) |
|---|---|---|---|---|
| | | Stems | | |
| T0 | 28.59$^b$ | 11.27$^b$ | | 11.40$^b$ |
| T1 | 32.84$^a$ | 12.29$^b$ | | 22.24$^a$ |
| T2 | 32.88$^a$ | 14.08$^a$ | | 22.25$^a$ |
| | | Leaves | | |
| T0 | 43.03$^c$ | 1.82$^b$ | | 9.11$^c$ |
| T1 | 60.92$^b$ | 4.31$^a$ | | 11.75$^b$ |
| T2 | 62.71$^a$ | 4.24$^a$ | | 22.48$^a$ |
| | | Roots | | |
| T0 | 12.44$^b$ | 1.76$^b$ | | 12.43$^c$ |
| T1 | 22.94$^a$ | 4.93$^a$ | | 17.79$^b$ |
| T2 | 22.79$^a$ | 4.89$^a$ | | 36.96$^a$ |

Means with same letter are not significantly different by DNMRT test at $p \leq 0.05$.

TABLE 11

Effect of treatments on N, P, and K use efficiency of maize plant at 56 days after planting

| Treatment | Stem | Leaves | Roots | Total |
|---|---|---|---|---|
| | | N (%) | | |
| T0 | nd | nd | nd | nd |
| T1 | 0.24$^d$ | 1.26$^a$ | 0.37$^a$ | 1.87$^a$ |
| T2 | 1.55$^b$ | 3.34$^b$ | 3.09$^b$ | 7.98$^b$ |
| | | P (%) | | |
| T0 | nd | nd | nd | nd |
| T1 | 0.32$^a$ | 0.31$^a$ | 0.40$^a$ | 1.03$^a$ |
| T2 | 1.65$^b$ | 1.89$^b$ | 0.49$^a$ | 4.03$^b$ |
| | | K (%) | | |
| T0 | nd | nd | nd | nd |
| T1 | 2.17$^a$ | 1.17$^a$ | 1.75$^a$ | 5.09$^a$ |
| T2 | 2.40$^a$ | 1.51$^b$ | 2.51$^b$ | 6.42$^b$ |

Means with same letter within column are not significantly different by DNMRT test at $p \leq 0.05$.

Amendment of urea with peat soil water significantly improved the retention of $NH_4^+$ and available $NO_3^-$ compared to urea alone. The findings of the present invention suggest that retention of $NH_4^+$ may be partly due to the effect of organic acids such as humic and fulvic acids in the peat water, which are noted for releasing $NH_4^+$ slowly. The ability of peat soil water to reduce soil pH determines the equilibrium between $NH_4^+$ and $NH_3$ in the system. The relative concentration of $NH_3$ decreased with decreasing pH whilst the $NH_4^+$ concentration increases and this minimizes $NH_3$ loss.

Urea amended with peat soil water in accordance with the present invention enhanced in N uptake and use efficiency of the test crop compared with that of urea alone. This was because the mixtures may have encouraged formation of $NH_4^+$ over $NH_3$. This was because the acidic nature of peat soil water may have acidified the soil surrounding urea-zeolite-peat soil water mixture because when the soil pH is less than 5.5, urea hydrolyzes slowly. Consequently, this process increased the volume soil which mixes with urea and the time required for hydrolysis to complete also increased. Upon urea hydrolysis, lower soil pH favoured the formation of $NH_4^+$ over $NH_3$.

INDUSTRIAL APPLICATION

The present invention provides controlled release of a plant treatment agent for plants. More specifically, the slow release liquid fertiliser formulated in accordance with the present invention can be suitably sprayed (foliar application), injected into soil, drenching, used in irrigation water, hydroponics or fertigation. The fertilizer of the present invention could be used to enhance plant growth being it cereals, vegetables, fruits and plantation crops. The materials used to prepare the formulation of the present invention are such that the formulation also possesses advantageous soil amendment properties.

The invention claimed is:

1. A slow release granule composition comprising a plant treatment agent, the granule composition comprising a mixture of acidic organic solution and urea,
   wherein the organic solution is liquid or waste water obtained from a peat material under pressure, and further wherein the peat material is fibric, hemic, or sapric; and
   wherein part of K and N of the granule composition are in the form of K-humate, K-fulvate, N-humate, and N-fulvate.

2. A slow release granule composition according to claim 1, wherein the organic solution is acidic.

3. A slow release granule composition according to claim 2, wherein the organic solution is of pH less than 4.

4. A slow release granule composition according to claim 1, wherein the plant treatment agent includes pesticides, gametocides, herbicides, defoliants, desiccants, plant-growth regulators, fertilizers, plant nutrients or mixtures thereof.

5. A slow release granule composition according to claim 1, wherein the organic solution comprises between 98% and 97% by weight in the slow release granule composition.

6. A slow release granule composition according to claim 1, wherein the urea comprises between 2% and 3% by weight in the slow release granule composition.

7. A method of treating a plant with a plant treatment agent, comprising applying a slow release granule composition as claimed in claim 1 to a plant.

8. A method according to claim 7, wherein the slow release granule composition is applied under a soil surface to promote plant growth.

9. A method to prepare a slow release granule composition comprising a plant treatment agent, wherein the method comprises the steps of:
   i. separating immiscible liquids or solids contained in a solution of liquid or waste water obtained from a peat material under pressure; and
   ii. equilibrating the solution of liquid or waste water obtained from the peat material obtained in step (i) with urea wherein the mixture is agitated at 180 rpm to 250 rpm to obtain a slow release granule composition, in which part of K and N are in the form of K-humate, K-fulvate, N-humate, and N-fulvate.

* * * * *